(12) United States Patent
Melvin et al.

(10) Patent No.: US 6,242,203 B1
(45) Date of Patent: Jun. 5, 2001

(54) TUMOR-SPECIFIC P450 PROTEIN

(75) Inventors: William Thomas Melvin; Graeme Ian Murray, both of Aberdeen; Michael Danny Burke, Leicester, all of (GB); William Frank Greenlee, Worcester, MA (US)

(73) Assignees: University of Aberdeen, Aberdeen (GB); University of Massachusetts, Boston, MA (US)

( * ) Notice: Subject to any disclaimer, the term of this patent is extended or adjusted under 35 U.S.C. 154(b) by 0 days.

(21) Appl. No.: 09/043,814

(22) PCT Filed: Sep. 25, 1996

(86) PCT No.: PCT/GB96/02368

§ 371 Date: Jan. 22, 1999

§ 102(e) Date: Jan. 22, 1999

(87) PCT Pub. No.: WO97/12246

PCT Pub. Date: Apr. 3, 1997

(30) Foreign Application Priority Data

Sep. 25, 1995 (GB) .................................... 9519490

(51) Int. Cl.[7] ........................ G01N 33/53; G01N 33/573; G01N 33/574; C07K 16/00

(52) U.S. Cl. .......................... 435/7.23; 435/7.1; 435/7.4; 435/7.92; 435/7.94; 530/388.8; 530/389.1; 530/38.6

(58) Field of Search ................................ 435/4, 7.1, 7.21, 435/7.23, 7.94

(56) References Cited

U.S. PATENT DOCUMENTS 5,422,243 * 6/1995 Jalkanen et al. ........................ 435/6

FOREIGN PATENT DOCUMENTS

| 43 09 344 | 9/1994 | (DE) | .............................. A61K/31/66 |
| 0 375 559 | 6/1990 | (EP) | .............................. C07J/31/00 |

OTHER PUBLICATIONS

Hohr et al . Archives of Biochem adn Biophysics, 321, 405–412, 1995.*
Brake et al., Proc. Annu. Meet. Am. Assoc. Cancer Res., vol. 36. pp. A1534, Mar. 1995.*
Bhattacharyya et al., The journal of Biological Chemistry, vol. 270, No. 19, pp. 11595–11602, May 1995.*
Albin et al., "Main Drug–metabolizing Enzyme Systems in Human Breast Tumors and Peritumoral Tissues", Cancer Research 53:3541–3546, 1993.
Batra et al., "Biology of Disease Oncogenes and Anti–oncogenes in Human Central Nervous System Tumors", Laboratory Investigation 71:621–637, 1994.
Buchmann et al., "Development of Cytochrome P–450–altered Preoplastic and Neoplastic Lesions during Nitrosamine–induced Hepatocarcinogenesis in the Rat", Cancer Research 47:2911–2918, 1987.
Buchmann et al., "Regulation and Expression of Four Cytochrome P–450 Isoenzymes, NADPH–cytochrome P450 Reductase, the Glutathione Transferases B and C . . . ", Carcinogenesis 6:513–521, 1985.
Capdevila et al., "Cytochrome P450 and the Arachidonate Cascade", FASEB J. 6:731–736, 1992.
Czerwinski et al., "Quantification of CYP2B7, CYP4B1, and CYPOR Messenger RNAs in Normal Human Lung and Lung Tumors", Cancer Research 54:1085–1091, 1994.
Dallman et al., "Semi–quantitative PCR for the Analysis of Gene Expression", PCR A Practical Approach eds J. McPherson, P. Quirke and G.R. Taylor (IRL Press, Oxford) pp. 215–224.
Ellington et al., "In Vitro Selection of RNA Molecules that Bind Specific Ligands", Nature 346:818–822, 1990.
Gonzalez et al., "Role of Human Cytochromes P450 in the Metabolic Activation of Chemical Carcinogens and Toxins", Drug Metabolism Reviews 26:165–183, 1994.
Guengerich, "Metabolic Activation of Carcinogens", Pharmac. Ther. 54:17–61, 1992.
Guengerich, "Oxidation of Toxic and Carcinogenic Chemicals by Human Cytochrome P–450 Enzymes", Chemical Research in Toxicology 4:391–407, 1991.
Guengerich, "Roles of Cytochrome P–450 Enzymes in Chemical Carcinogenesis and Cancer Chemotherapy", Cancer Research 48:2946–2954, 1988.
Horikoshi et al., "Quantitation of Thymidylate Synthase, Dihydrofolate Reductase, and DT–Diaphorase Gene Expression in Human Tumors Using the Polymerase Chain Reaction", Cancer Research 52:108–116, 1992.
Jaiswal et al., "Human Dioxin–Inducible Cytochrome $P_1$–450: Complementary DNA and Amino Acid Sequence", Science 228:80–83, 1985.
Jaiswal et al., "Human $P_3$450: cDNA and Complete Amino Acid Sequence", Nucleic Acid Research 14:6773–6774, 1986.

(List continued on next page.)

Primary Examiner—Karen M. Hauda
Assistant Examiner—Shin-Lin Chen
(74) Attorney, Agent, or Firm—Fish & Richardson P.C.

(57) ABSTRACT

The discovery that Cyp1B1 protein is detectable in a wide range of human cancers of different histogenetic types, but is not detectable in non-cancerous tissues, gives rise to diagnostic methods for detecting tumors based on this protein as a marker, and to the possibility of tumor therapies involving the protein. A diagnostic method may include the steps of: (a) obtaining from a patient a tissue sample to be tested for the presence of cancer cells; (b) producing a prepared sample in a sample preparation process; (c) contacting the prepared sample with an antibody that reacts with human Cyp1B1 protein; and (d) detecting binding of the antibody to CYP1B1 protein in the prepared sample.

20 Claims, 2 Drawing Sheets

OTHER PUBLICATIONS

Janot et al., "Principal Xenobiotic–metabolizing Enzyme Systems in Human Head and Neck Squamous Cell Carcinoma", Carcinogenesis 14:1279–1283, 1993.

Kaminsky et al., "Small Intestinal Cytochromes P450", Crit. Rev. Toxicol. 21:407–422, 1992.

Kawajiri et al., "P450 and Human Cancer", Jpn. J. Cancer Research. 82:1325–1335, 1991.

Kivisto et al., "The Role of Human Cytochrome P450 Enzymes in the Metabolism of Anticancer Agents: Implications for Drug Interactions", Brit. J. Clin. Pharmacol. 40:523–530, 1995.

Krontiris, "Molecular Medicine Oncogenes", The New England Journal of Medicine 333:303–306, 1995.

Le Blanc et al., "Interaction of Anticancer Drugs with Hepatic Monooxygenase Enzymes", Drug Metabolism Reviews 20:395–439, 1989.

Laemmli, "Cleavage of Structural Proteins During the Assembly of the Head of Bacteriophage T4", Nature 227:680–685, 1970.

Lowry et al., "Protein Measurement with the Folin Phenol Reagent", J. Biol. Chem. 193:265–275, 1951.

McKay et al., "Expression of Cytochrome P450 CYP1B1 in Breast Cancer", FEBS Letters 374:270–272, 1995.

McKay et al., "Localization of Microsomal Epoxide Hydrolase in Normal and Neoplastic Human Kidney", The Journal of Histochemistry and Cytochemistry 43:615–620, 1995.

Massaad et al., "Comparison of Mouse and Human Colon Tumors with Regard to Phase I and Phase II Drug–Metabolizing Enzyme Systems", Cancer Research 52:6567–6575, 1992.

Mekhail Ishak et al., "Implications for Therapy of Drug–metabolizing Enzymes in Human Colon Cancer", Cancer Research 49:4866–4869, 1989.

Miller, "Molecular Biology and Steriod Hormone Synthesis", Endocrine Rev. 9:265–318, 1988.

Murray et al., "Cytochrome P450 Expression is a Common Molecular Event in Soft Tissue Sarcomas", Journal of Pathology 171:49–52, 1993.

Murray et al., "Cytochrome P450 Expression in Oesophageal Cancer", Gut 35:599–603, 1994.

Murray et al., "Expression of Cytochrome P450IA in Breast Cancer", Br. J. Cancer 63:1021–1023, 1991.

Murray et al., "Commentary Immunohistochemistry of Drug–Metabolizing Enzymes", Biochemical Pharmacology 50:895–903, 1995.

Nedelcheva et al., "P450 in the Rat and Man: Methods of Investigation, Substrate Specificities and Relevance to Cancer", Xenobiotica 24:1151–1175, 1994.

Nelson et al., "P450 Superfamily: Update on New Sequences, Gene Mapping, Accession Numbers and Nomenclature", Pharmacogenetics 6:1–42, 1996.

Oliw, "Oxygenation of Polyunsaturated Fatty Acids by Cytochrome P450 Monooxygenases", Prog. Lipid Res. 33:329–354, 1994.

Otto et al., "A Novel Adrenocorticotropin–Inducible Cytochrome P450 from Rat Adrenal Microsomes Catalyzes Polycylic Aromatic Hydrocarbon Metabolism", Endocrinology 129:970–982, 1991.

Peters et al., "Expression of Drug–Metabolizing Enzymes and P–170 Glycoprotein in Colorectal Carcinoma and Normal Mucosa", Gastroenterology 103:448–455, 1992.

Ponz de Leon, "Oncogenes and Tumor Suppressor Genes", Recent Res. Cancer Res. 136:35–47, 1994.

Roomi et al., "A Common Biochemical Pattern in Preneoplastic Hepatocyte Nodules Generated in Four–Different Models in the Rat", Cancer Research 45:564–571, 1985.

Schuetz et al., "Expression of Cytochrome P450 3A in Amphibian, Rat, and Human Kidney", Archives of Biochemistry and Biophysics, 294:206–214, 1992.

Schweikl et al., "Expression of CYP1A1 and CYP1A2 Genes in Human Liver", Pharmacogenetics 3:239–249, 1993.

Sesardic et al., "Differential Expression and Regulation of Members of the Cytochrome P450IA Gene Subfamily in Human Tissues", Carcinogenesis 11:1183–1188, 1990.

Spink et al., "17β–Estradiol Hydroxylation Catalyzed by Human Cytochrome P450 1A1: A Comparison of the Activities Induced by 2,3, . . . ", Archives of Biochemistry and Biophysics 293:342–348, 1992.

Sutter et al., "Complete cDNA Sequence of a Human Dioxin–Inducible mRNA Identifies a New Gene Subfamily of Cytochrome P450 That Maps to Chromosome 2", The Journal of Biological Chemistry 269:13092–13099, 1994.

Taylor et al., "Cytochrome P450 1B1 Expression in Human Malignant Tumors", Biochemical Society Transactions 24:328S, 1996.

Toussaint et al., "Main–Drug– and Carcinogen–metabolizing Enzyme Systems in Human Non–Small Cell Lung Cancer and Peritumoral Tissues", Cancer Research 53:4608–4612, 1993.

Towbin et al., "Electrophoretic Transfer of Proteins from Polyacrylamide Gels to Nitrocellulose Sheets: Procedure and Some Applications", Proc. Natl. Acad. Sci. USA 76:4350–4354, 1979.

Wang et al., "Hypoxia–inducible Factor 1 is a Basic–helix–loop–helix–PAS Heterodimer Regulated by Cellular $O_2$ Tension", Proc. Natl. Acad. Sci. USA 92:5510–5514, 1995.

Waziers et al., "Drug–metabolizing Enzyme Expression in Human Normal, Peritumoral and Tumoral Colorectal Tissue Samples", Carcinogenesis 12:905–909, 1991.

Weaver et al., "A Comparative Study of Constitutive and Induced Alkoxyresorufin O–Dealkylation and Individual Cytochrome P450 Forms in Cynomolgus Monkey . . . ", Biochemical Pharmacology 47:763–773, 1994.

Weaver et al., "Cytochrome P450 2C9 is Responsible for Hydroxylation of the Naphthoquinone Antimalarial Drug 58C80 in Human Liver", Biochemical Pharmacology 46:1183–1197, 1993.

Whitlock et al., "Induction of Cytochrome P4501A1: A Model for Analyzing Mammalian Gene Transcription", FASEB J. 10:809–818, 1996.

Williamson, "Aptly Named Aptamers Display Their Aptitude", Nature 382:112–113, 1996.

Wrighton et al., "The Human Hepatic Cytochromes P450 Involved in Drug Metabolism", Critical Reviews in Toxicology 22:1–21, 1992.

\* cited by examiner

SEQUENCE LISTING

<160> NUMBER OF SEQ ID NOS: 4

<210> SEQ ID NO: 1
<211> LENGTH: 20
<212> TYPE: DNA
<213> ORGANISM: Homo sapiens

<400> SEQUENCE: 1
aactctccat caggtgaggt                                           20

<210> SEQ ID NO: 2
<211> LENGTH: 21
<212> TYPE: DNA
<213> ORGANISM: Homo sapiens

<400> SEQUENCE: 2
taaggaagta taccagaagg c                                         21

<210> SEQ ID NO: 3
<211> LENGTH: 30
<212> TYPE: DNA
<213> ORGANISM: Homo sapiens

<400> SEQUENCE: 3
tgacggggtc acccacactg tgcccatcta                                30

<210> SEQ ID NO: 4
<211> LENGTH: 30
<212> TYPE: DNA
<213> ORGANISM: Homo sapiens

<400> SEQUENCE: 4
ctagaagcat ttgcggtgga cgatggaggg                                30

TUMOR-SPECIFIC P450 PROTEIN

Work on this invention was supported in part by NIH Grant No. ES-07009. Therefore, the U.S. government may have certain rights in the invention.

FIELD OF THE INVENTION

This invention relates to tumour diagnosis and therapy, and to materials and methods for use therein.

More particularly, the invention is based on the identification of a cytochrome P450 form, specifically CYP1B1, in a wide range of tumours, with a high frequency of expression in each type, and proposes the use of this enzyme as a tumour marker, and as the basis of a selective therapeutic approach involving the design of drugs, eg which are activated to a cytotoxic form by the action of CYP1B1.

BACKGROUND TO THE INVENTION

The major goal of cancer chemotherapy is the development of anti-cancer drugs that are effective in a wide range of cancers and produce no toxic effects in normal tissues. The target of such drugs should be expressed only in tumour cells and not normal cells. However, to date, no such tumour specific target, general to all types of cancers, has been identified.

The cytochromes P450 are a multi-gene family of constitutive and inducible enzymes, which have a central role in the oxidative metabolic activation and detoxification of both a wide range of xenobiotics (2–4) and several groups of endogenous compounds active in cell regulation and cell signalling including arachidonic acid (5), steroid hormones (6) and fatty acids (7). The major families of P450 involved in xenobiotic metabolism each consist of several individual forms with different regulatory mechanisms and substrate specificities (2). The majority of P450s are primarily expressed in liver (2) although individual P450 forms are also expressed in specific extra-hepatic tissues (8) including small intestine, kidney and lung.

The human CYP1 gene family (individual P450 forms are identified by the prefix CYP in accordance with the current P450 nomenclature (3)), which is one of the major P450 families involved in the metabolism of xenobiotics, is now known to consist of three individual forms classified into two sub-families. The CYP1A subfamily contains two highly homologous and well characterised but distinct members. CYP1A1 (9) and CYP1A2 (10). CYP1A1 is an inducible P450 expressed primarily in extraheptic tissues (11) while CYP1A2 is a major form of P450 that is constitutively expressed in liver (12). Recently a second human CYP1 subfamily has been identified which to date contains one member, CYP1B1 (1). This P450 is dioxin-inducible, and sequence analysis of CYP1B1 shows 40% homology with both CYP1A1 and CYP1A2. Although CYP1B1 is assigned to the CYP1 family on the basis of its sequence, it appears to be structurally distinct from both CYP1A1 and CYP1A2.

Several forms of P450 are considered to have an important role in tumour development since they can metabolise many potential carcinogens and mutagens (13). Moreover, P450 activity may influence the response of established tumours to anti-cancer drugs; several cancer chemotherapeutic agents can be either activated or detoxified by this enzymes system (14). The presence of individual forms of P450 had previously been investigated in different types of cancer including breast cancer (15), lung cancer (16), colon cancer (17) and head and neck cancer (18) to determine if intra-tumour metabolism of anti-cancer agents by P450 could occur and thus influence the response of tumours to these agents. These studies have generally shown that the level of the P450 forms investigated is significantly reduced or absent in tumours when compared with the adjacent normal tissue in which the tumours have developed. However, our recent studies of several different types of cancer (19) including breast cancer, oesophageal cancer and soft tissue sarcomas have shown that there may be tumour-specific expression of a CYP1 form of P450.

Although CYP1B1 mRNA had previously been identified by Northern blotting in several normal human tissues (1), the presence CYP1B1 protein itself had not been demonstrated.

SUMMARY OF THE INVENTION

The present invention is based on the discovery that CYP1B1 is a tumour-specific form of P450, present in a wide range of malignant tumours and not detected in normal tissues.

Accordingly, a first aspect of the present invention provides a method for the identification of tumour cells, which method comprises the use of a recognition agent, for example an antibody, recognising CYP1B1 protein to contact a sample of tissues, cells, blood or body product, or samples derived therefrom, and screening for a positive response. The positive response may for example be indicated by an agglutination reaction or by a visualisable change such as a colour change or fluorescence, eg immunostaining, or by a quantitative method such as in use of radio-immunological methods or enzyme-linked antibody methods.

The method therefore typically includes the steps of (a) obtaining from a patient a tissue sample to be tested for the presence of cancer cells; (b) producing a prepared sample in a sample preparation process; (c) contacting the prepared sample with a recognition agent, such as an antibody, that reacts with human CYP1B1 protein; and (d) detecting binding of the recognition agent to CYP1B1 protein, if present, in the prepared sample. The human tissue sample can be from for example the bladder, brain, breast, colon, connective tissue, kidney, lung, lymph node, oesophagus, ovary, skin, stomach, testis, and uterus.

A preferred sample preparation process includes tissue fixation and production of a thin section. The thin section can then be subjected to immunohistochemical analysis to detect binding of the recognition agent to CYP1B1 protein. Preferably, the immunohistochemical analysis includes a conjugated enzyme labelling technique. A preferred thin section preparation method includes formalin fixation and wax embedding. Alternative sample preparation processes include tissue homogenization, and preferably, microsome isolation. When sample preparation includes tissue homogenization, a preferred method for detecting binding of the antibody of CYP1B1 protein is Western blot analysis. Alternatively, an immunoassay can be used to detect binding of the antibody to CYP1B1 protein. Examples of immunoassays are antibody capture assays, two-antibody sandwich assays, and antigen capture assays. Preferably, the immunoassays is a solid support-based immunoassay. When Western blot analysis or an immunoassay is used, preferably it includes a conjugated enzyme labelling technique.

Although the recognition agent will conveniently be an antibody, other recognition agents are known or may become available, and can be used in the present invention. For example, antigen binding domain fragments of antibodies, such as Fab fragments, can be used. Also, so-called RNA aptamers may be used (36, 37). Therefore, unless the context specifically indicates otherwise, the term "antibody" as used herein is intended to include other recognition agents. Where antibodies are used, they may be polyclonal or monoclonal. Optionally, the antibody can produce by a method so that it recognizes a preselected epitope of said CYP1B1 protein.

A second aspect of the invention lies in the presence of CYP1B1 protein selectively in tumours, eg in kidney tumours and not normal renal tissue, combined with the absence of CYP1B1 protein expression in normal liver, which provides a mechanism for the selective targeting of anti-cancer drugs based on CYP1B1 metabolism in tumours. Drugs can be designed for, or screened for, specific metabolism by CYP1B1 in tumours whereby this metabolism converts a non-toxic moiety into a toxic one, which kills or inhibits the tumour or makes it more susceptible to other agents.

A third aspect of the invention provides for the targeting of cytotoxic drugs or other therapeutic agents, or the targeting of imaging agents, by virtue of their recognition of CYP1B1 epitopes on the surface of a tumour cell, whether as part of the complete CYP1B1 protein itself or in some degraded form such as in the presentation on the surface of a cell bound to a MHC protein.

Another aspect of the invention provides stimulation of the immune system of cancer patients, for example by activating cytotoxic or helper T-cells which recognise CYP1B1 epitopes so as to implement a cell-mediated or humoral immune response against the tumour. The activation of the immune system can be achieved by immunisation with CYP1B1 sequences.

Because the expression of CYP1B1 is very common in tumours of many different types, it is likely that this enzyme performs an essential function for the tumour cells, for example by inactivating endogenous anti-tumour compounds such as 2-methoxyestradiol. Consequently, another aspect of the invention is the reduction of CYP1B1 levels in tumour cells, for example by the use of suicide inhibitors or by using antisense RNA methods to decrease the synthesis of the protein. Down-regulation of the CYP1B1 promoter could also achieve the reduction of CYP1B1 levels.

DETAILED DESCRIPTION OF THE INVENTION

Figure 1:
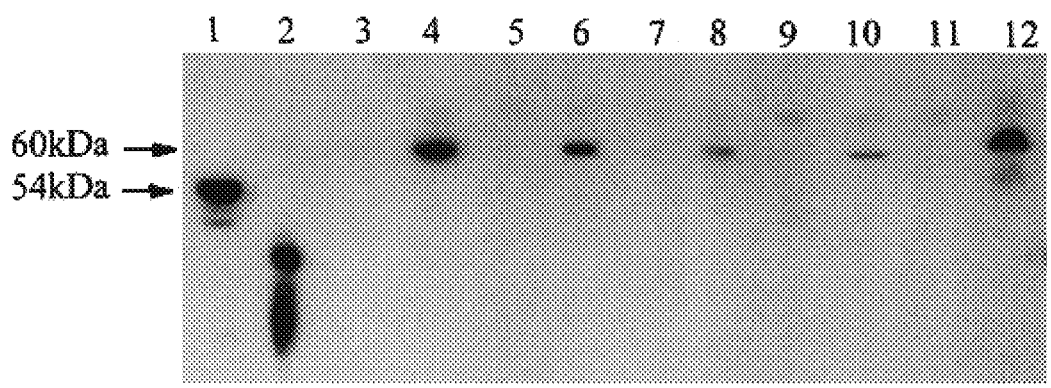
FIG. 1 shows SDS-PAGE and immunoblotting procedures using an anti-CYP1B1 antibody to look for CYP1B1 protein in normal and tumorous kidney tissue and in normal liver tissue.

Expression of CYP1B1 was investigated in different types of cancers that had developed in a broad range of different anatomical sites (bladder, breast, colon, kidney, lung, oesophagus, ovary, skin, stomach, uterus, bone and connective tissue, lymph node, brain and testis). Primary malignant tumours of these tissues constitute different histogenetic types (carcinomas, lymphomas, sarcomas, neuro-epithelial tumours and germ cell tumours) each with a different biological behaviour. These tumours also represent a range of both common and less common types of cancer. The presence of CYP1B1 was also investigated in a wide variety of normal tissues.

Immunohistochemistry for CYP1B1 showed that in all the different types of tumour there was strong immunoreactivity for CYP1B1. CYP1B1 immunoreactivty was localised specifically to tumour cells. Non-tumour cells including stromal cells, inflammatory cells, and endothelial cells present in the sections of tumour showed no immunoreactivity for CYP1B1.

There was no significant intra-tumour heterogeneity of CYP1B1 immunoreactivity and only in five out of 133 tumours was CYP1B1 not detected. There was no immunoreactivity for CYP1B1 in any of the normal tissues studied which included liver, kidney, small intestine and lung.

The absence or low level of individual forms of P450 in most studies of human cancer (15–18), combined with extrapolation from studies of rodent hepatic carcinogenesis (25), had led to the general belief that tumour cells do not significantly express P450. However, we have now shown that CYP1B1 is expressed in a wide variety of malignant tumours of different histogenetic types and is not present in normal tissues, indicating that this P450 is a tumour specific form of P450. Tumours are composed of a variable proportion of tumour cells and non-tumour cells. To identify that a protein is tumour specific, it is important to demonstrate that the protein is localised only to tumour cells. Immunohistochemistry allows the direct visualisation of tumour cells and has the spatial resolution to separate tumour cells from non-tumour cells. Furthermore, it is important to show there has been no differential degradation of proteins in normal tissue samples compared with tumour samples, and immunoblotting for $\beta$-actin (as a positive control protein) showed it to be present in every normal and tumour sample indicating there was no protein degradation. In addition, Coomassie blue staining of the polyacrylamide gels showed no evidence of protein degradation. Moreover, immuno-histochemistry of the tumour samples provides its own internal control as sections of tumour contain non-tumour cells.

The presence of CYP1B1 in many types of tumour suggests that this P450 may have a crucial endogenous function in tumour cells and CYP1B1 may contribute to drug resistance that is observed in many types of tumour. CYP1B1 is also likely to be important in tumour development and progression. Its identification in a diverse range of cancers of different histogenetic types and is absence from normal tissues appears to make CYP1B1 one of the common changes of a gene product in malignancy (26).

A previous investigation (1) found mRNA in normal tissues. In some tumours, increased (2–4x) mRNA was found compared with normal. This might be due to increased transcription mediated by hypoxia inducible factor. This is a novel heterodimeric transcription factor which is induced by hypoxia, and the stimulus in this case may be the hypoxic micro-environment that can exist in tumours, and this factor can have as one of its components the Ah receptor nuclear translocator (27). However, regulation of other forms of P450 is complex (2, 28) and the regulation of CYP1B1 in tumours is likely to be complex also, with multiple mechanisms including transcriptional and post-transcriptional factors involved.

The tumour-specific expression of CYP1B1 has important consequences for both the diagnosis and treatment of cancer. New diagnostic procedures based on the presence of CYP1B1 in cancer cells can be developed, while the expression of CYP1B1 in tumour cells provides a molecular target for the development of new anti-cancer drugs that are selectively activated by CYP1B1 in tumour cells. Since CYP1B1 is found in a wide range of tumours it would be expected that such drugs would be effective in treating many different types of cancer. An important feature is that it would be anticipated these drugs would not be associated with the systematic toxicity that limits the use of current anti-cancer drugs as CYP1B1 is not present in normal tissues especially liver, small intestine and kidney that are the main tissues involved in drug metabolism. Thus, a major problem to targeting anti-cancer drugs at tumours based on their selective activation by P450 has been marked hepatic P450 metabolism of drugs resulting in decreased bioavailability and/or undue toxicity. The absence of CYP1B1 protein in liver overcomes this problem.

As regards tumour diagnosis, numerous methods for using antibodies to detect a specific protein, including CYP1B1, in a biological sample are known and can be used in the present invention. Any of the various antibody methods can be used alone in practising the present invention. If desired, two or more methods can be used to complement one another.

A preferred method for use in the present invention is immunohistochemical analysis. Immunohistochemical analysis advantageously avoids a dilution effect when relatively few cancer cells are in the midst of normal cells. An early step in immunohistochemical analysis is tissue fixation, which preserves proteins in place within cells. This prevents substantial mixing of proteins from different cells. As a result, surrounding normal cells do not diminish the detectability of CYP1B1-containing cancer cells. This is in contrast to assay methods that involve tissue homogenization. Upon tissue homogenization, CYP1B1 protein from cancer cells is mixed with proteins from any surrounding normal cells present in the tissue sample. The concentration of CYP1B1 protein is thus reduced in the prepared sample, and it can fall below detectable limits. Immunohistochemical analysis has at least three other advantages. First, it requires less tissue than is required by alternative methods such as Western blot analysis or immunoassay. Second, it provides information on the intracellular localization and distribution of immunoreactive material. Third, information on cell morphology can be obtained from the same thin section used to test for the presence of CYP1B1 protein. Preferably, when immunohistochemical analysis is employed in the practice of this invention, several thin sections from each tissue sample are prepared and analysed. This increases the chances of finding small tumours.

Another preferred antibody method for use in the present invention is Western blot analysis, ie sodium dodecyl sulfate-polyacrylamide gel electrophoresis (SDS-PAGE), followed by immunoblotting. Sample preparation for Wester blot analysis includes tissue homogenization, and optionally isolation of microsomes. Western blot analysis has the advantage of detecting immunoreactivity on proteins that have been separated with high resolution, according to (apparent) molecular weight.

Immunoassays such as antibody capture assays, two-antibody sandwich assays, and antigen capture assays can also be used in the present invention. Sample preparation for immunoassays include tissue homogenization, and optionally isolation of microsomes. Immunoassays have the advantage of enabling large numbers of samples to be tested relatively quickly, and they offer quantitative precision.

Principles and practice of immunohistochemistry, Western blot analysis, and immunoassays are well known. One of ordinary skill in the art can select suitable protocols and carry out immunohistochemical analysis. Western blot analysis, or an immunoassay, in the practice of the present invention (30).

Experimental details

1. Preparation of antibodies

As already noted, the diagnostic aspects of the present invention can conveniently use an antibody that recognizes human CYP1B1. Antibody specificity for CYP1B1 protein is preferable, but not required. Preferably, any non-CYP1B1 protein recognized by the antibody is readily distinguished from CYP1B1, eg, according to apparent molecular weight on a Western blot. With selection of an appropriate assay protocol, which is within ordinary skill in the art, the invention can be practised with a polyclonal antibody or a monoclonal antibody.

A polyclonal antibody or monoclonal antibody suitable for use in the present invention can be obtained according to conventional procedures (30). Preparation of antibodies that react with CYP1B1 protein is known (31). Procedures for obtaining antibodies that react with human CYP1B1 protein can be carried out using a preparation of non-human CYP1B1 protein, eg, murine CYP1B1 protein. A CYP1B1 protein preparation suitable for eliciting antibodies useful in the present invention can be obtained according to various procedures, including those described (31).

Antibodies useful in the present invention can be obtained by immunizing an animal with a preparation containing intact CYP1B1 protein. Alternatively, useful antibodies can be obtained by immunizing an animal with a polypeptide or oligopeptide corresponding to one or more epitopes on the CYP1B1 protein.

Preparation

To prepare an antibody according to the latter approach, two 15-mer peptides corresponding to epitopes on the human CYP1B1 protein were synthesized. Each corresponded to a different putative surface loop region of the CYP1B1 enzyme. The first peptide (designated 217A) consisted of 14 amino acids, ie, ESLRPGAAPR DMMD (SEQ ID NO:1). Peptide 217A represented amino acid positions 312–325 of the deduced amino acid sequence. A carboxy terminal cysteine was included for use in a conjugation reaction. The second peptide (designated 218A) consisted of 14 amino acids, ie, EKKAAGDSHG GGAR (SEQ ID NO:2). Peptide 218A represented positions 332–345 of the deduced amino acid sequence. A carboxy terminal cysteine was added for use in a conjugation reaction. Each of these peptides was conjugated directly to KLH.

Male New Zealand rabbits were immunized at several anatomical sites using 100 $\mu$g of the 217A peptide conjugate or the 218A peptide conjugate. The conjugates were dissolved in 300 $\mu$l of PBS mixed with 300 $\mu$l of Freund's Complete Adjuvant. Three weeks after the initial immunization, the rabbits were boosted with 50 $\mu$g of one of each of the conjugates (contained in 300 $\mu$l PBS mixed with 300 $\mu$l of Freund's Incomplete Adjuvant, injected in several sites). One week later (four weeks after the initial injection), the rabbits were boosted again, using the same protocol. One week after this second boost, the first serum sample was collected. Rabbits were subsequently boosted, and serum samples were collected, weekly. Serum samples were screened for anti-CYP1B1 titre and specificity by Western blotting against a human CYP1B1-maltose binding fusion protein expressed in *E. coli*, and human CYP1B1 protein expressed in COS-1 cells.

Anti-CYP1B1 IgG was purified by immunoaffinity chromatography. The chromatography was carried out using the appropriate CYP1B1 peptide linked directly to a commercial N-hydroxysuccinamide ester of a derivatized, cross-linked agarose gel bead support (AffiGel 10; Biorad, Richmond, Calif.). Conjugation and chromotography were performed according to the vendor's recommended protocols.

2. Detection of CYP1B1 protein and its mRNA

In general in the experiments that follow, samples of normal tissue were obtained from tissue specimens that were removed from patients undergoing surgery for malignant disease. Normal liver, stomach and small intestine were also obtained from organ transplant donors. All the tissue samples were processed immediately after excision to prevent any degradation of protein or mRNA and ensure no deterioration in tissue morphology. We have previously shown that human liver obtained in this way shows no loss or degradation of individual forms of hepatic P450 (20). Tissue blocks for immuno-histochemistry were fixed in 10% neutral buffered formalin for 24 hours and then embedded in wax, while tissue samples for immunoblotting and mRNA analyses were rapidly frozen in liquid nitrogen and stored at −80° C. prior to use.

The presence of CYP1B1 protein in tissue samples was investigated using immunohistochemistry (21) and sodium dodecyl sulphate polyacrylamide gel electrophoresis (SDS-PAGE) combined with immunoblotting (22). Immunohistochemistry ensures the identification of specific types of cells containing CYP1B1 and is an idea technique for investigating the presence of CYP1B1 in tumour cells as tumours are composed of a variable proportion of tumour cells and non-tumour cells.

Immunohistochemistry was used to determine the cellular localisation and distribution of CYP1B1 and was performed on formalin fixed wax embedded sections using two antibodies which recognise CYP1B1. Sites of immunoreactivity were detected using an alkaline phosphatase anti-alkaline phosphatase (APAAP) technique (21). Samples of tumour and normal tissue were fixed in 10% neutral buffered formalin for 24 hour and then embedded in wax. Sections were cut on to glass slides and for immunohistochemistry sections of tumours and normal tissues were dewaxed in xylene, rehydrated in alcohol and then washed sequentially in cold water and 0.05M Tris-HCl (pH 7.6) containing 0.15M sodium chloride (TBS). The sections were then immunostained with the CYP1B1 antibodies. Subsequently, monoclonal mouse anti-rabbit immunoglobulin (1/100, Dako Ltd, High Wycombe, Bucks; UK), rabbit anti-mouse immunoglobulin (1/100, Dako) and mouse monoclonal APAAP (1/100, Dako) were sequentially applied to the tissue sections for 30 minutes each. Between antibody applications the sections were washed with TBS to remove unbound antibody. Sites of bound alkaline phosphatase were identified using brom-chloro-indolyl phosphate and nitro blue tetrazolium as the enzyme substrate. After incubating the sections for 30 minutes at room temperature, the reaction was stopped by washing the sections in cold tap water. The slides were then air-dried and mounted in glycerine jelly. The sections were examined using bright field light microscopy in order to establish the presence or absence of immunostaining, and its distribution.

SDS-PAGE and immunoblotting was followed by enhanced chemiluminescenece (ECL) technique as described below. Immunoblotting was also performed with a monoclonal antibody to β-actin (clone no. AC-15, Sigma, Poole, Dorset, UK) to show the presence of a positive control protein in tumour and normal samples and indicate that there was no evidence of protein degradation in any of the tissue samples.

The presence of CYP1B1 in each tumour that showed CYP1B1 by immunohistochemistry, and the absence of detectable CYP1B1 in normal tissues, was confirmed by Western blot analysis. The proteins subjected to Western blot analysis were from isolated microsome preparations.

Microsomes were prepared essentially as described (32). Tissue samples were thawed in 25 ml 0.01M Tris-HCl buffer, pH 7.4, containing 1.15% KCl before being homogenized in 0.01 M Tris-HCl buffer, pH 7.4, containing 0.25 M sucrose, 15% glycerol, using an Ultra-Turrax homogenizer (type TP 18/2; Janke and Kunkel AG, Staufen Breisgau, Germany). After centrifugation at 15,000×g for 20 min, the supernatant was removed and recentrifuged at 116,000×g for 50 min. The pellet was resuspended a first time in 0.1M Tris-HCl buffer, pH 7.4, containing 15% glycerol, 1 mM EDTA, and recentrifuged at 116,000×g for 50 min. The pellet was resuspended a second time in Tris-HCl-glycerol-EDTA buffer. Microsomal protein concentration was determined (34).

A discontinuous polyacrylamide gel system, as described (33) with modifications (32), was employed for separation of proteins in the microsomes. 20 $\mu$l of a 1 mg/ml preparation of normal samples, and 40 $\mu$l of a 0.5 mg/ml preparation of tumour samples, in 0.125M Tris-HCl, pH 6.8, containing 2.35% (w/v) sodium dodecyl sulfate, 5% (v/v) 2-mercaptoethanol, and 0.005% bromophenol blue tracking dye were loaded onto the gel. 10 $\mu$l of a 1 mg/ml preparation of human liver microsomes were used as positive controls. Samples were run on a 10% non-gradient gel at 30 mA.

Following SDS-PAGE, resolved proteins were blotted onto a nitrocellulose membrane (Schleicher & Schuell; Dassel, Germany) overnight as described (35). Nonspecific binding sites were blocked with PBS containing 2% (w/v) nonfat milk, 0.05% (v/v) TWEEN 20™ for 30 minutes at room temperature, with continuous shaking. This buffer was also used for washing stages. The nitrocellulose membrane was then incubated with CYP1B1-specific antibody (1:1000) for 90 minutes and goat anti-rabbit immunoglobulin horseradish peroxidase conjugate (1:2000 Bio-Rad Laboratories, Hemel Hempstead, Herts, UK) for 60 minutes. The membrane was washed for three successive 15-minute periods and one 60-minute period after each incubation to remove unbound antibody. Bound horseradish peroxidase was then visualized with an Enhanced Chemiluminescence (ECL) kit (Amersham International, Aylesbury, Bucks, UK). Detection was carried out as described in the ECL protocol, with the X-ray film (Hyperfilm-ECL; Amersham) being exposed for 30 seconds.

EXAMPLE 1

Expression of CYP1B1 in normal kidney and kidney tumours were investigated.

Nephrectomy specimens (n=10) excised from primary renal cell carcinoma were used. Samples or normal kidney were taken at least several centimetres distant from the edge of each tumour, and only macroscopically viable tumour was sampled. Normal human livers (n=5) were obtained from renal transplant donors and stored at −80° C. prior to use.

Microsomes of normal kidney, kidney tumours and normal liver were prepared and subjected to the SDS-PAGE and immunoblotting procedures in an enhanced chemiluminescence technique (21, 22) using an anti-CYP1 polyclonal antibody. Recognition of human CYP1B1 was demonstrated using a maltose-binding recombinant CYP1B1 fusion protein expressed in E. coli. Expressed CYP1A1 and CYP1A2 were supplied by Dr C L Crespi, Gentest Corp, Mass., USA. The results are shown in FIG. 1: lane 1 human liver, lane 2 expressed recombinant CYP1B1 protein lanes 3, 5, 7, 9, 11 normal kidney samples, lanes 4, 6, 8, 10, 12 corresponding kidney tumours. The same amount of microsomal protein (30 μg) was loaded into each lane, thus allowing direct comparison between the kidney and liver samples.

As shown in FIG. 1, the kidney tumours and expressed CYP1B1 show a single immunoreactive band at 60 kDa corresponding to the molecular weight of expressed CYP1B1. In normal kidney none of the samples showed an immunoreactive band at 60 kDa. In addition, none of the kidney tumours or normal kidney samples showed the presence of CYP1A1.

Immunoblotting of liver samples an immunoreactive band at 54 kDa corresponding to the molecular weight of CYP1A2. The intensity of the band at 54 kDa showed liver-to-liver variation, whereas there was no CYP1B1 immunoreactive band at 60 kDa in any of the liver samples.

EXAMPLE 2

The expression of CYP1B1 was also investigated in breast cancer using immunoblotting.

Samples of breast tissue were obtained from patients undergoing surgery either for primary breast cancer or non-neoplastic breast disease. Immunoblotting was performed on breast cancers obtained from six patients (age range 45–67; three non-smokers, information not available for three patients), and histologically all these tumours were carcinomas of no special type. The tissue samples were frozen in liquid nitrogen and stored at −80° C. prior to analysis.

Figure 2:
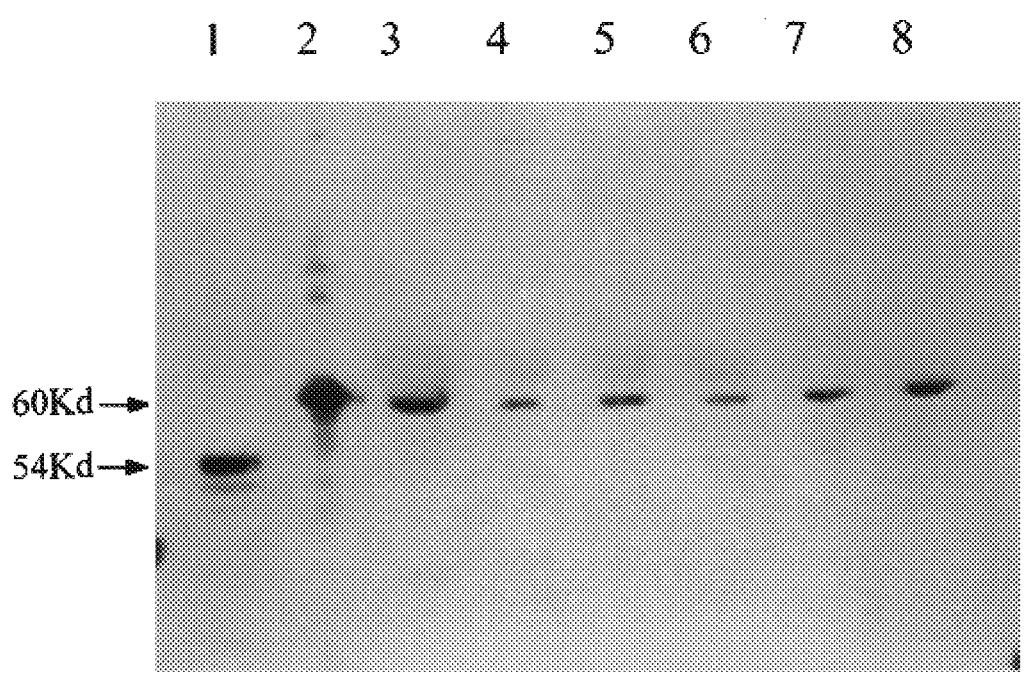
FIG. 2 shows SDS-PAGE and immunoblotting to detect CYP1B1 protein in breast tumour and in normal liver tissue.

SDS-PAGE and immunoblotting were carried out as described previously. CYP1B1 was detected using the anti-CYP1 polyclonal antibody referred to above. The results are shown in FIG. 2; lane 1 human liver, lane 2 expressed CYP1B1, lanes 3–8 breast tumors. As can be seen, a single protein band of molecular weight 60 kDa corresponding to the molecular weight of the expressed CYP1B1 protein was identified. As previously, CYP1B1 was not detectable in the liver sample, but CYP1A2 was detected.

EXAMPLE 3

Immunohistochemistry was used to demonstrate the presence of CYP1B1 specifically in a variety of normal and tumour tissues. The results are shown in Table 1 and in FIG. 3.

Immunohistological localisation of CYP1B1 was investigated in tumours and normal tissues from invasive ductal carcinoma of the breast, endometrial adenocarcinoma, transitional cell carcinoma of the bladder, diffuse high grade malignant lymphoma, high grade astrocytoma of the brain, soft tissue sarcoma (malignant fibrous histocytoma), normal liver, normal kidney, normal small intestine. The antibody used was the 218A anti-CYP1B1 polyclonal antibody described above.

Figure 3:
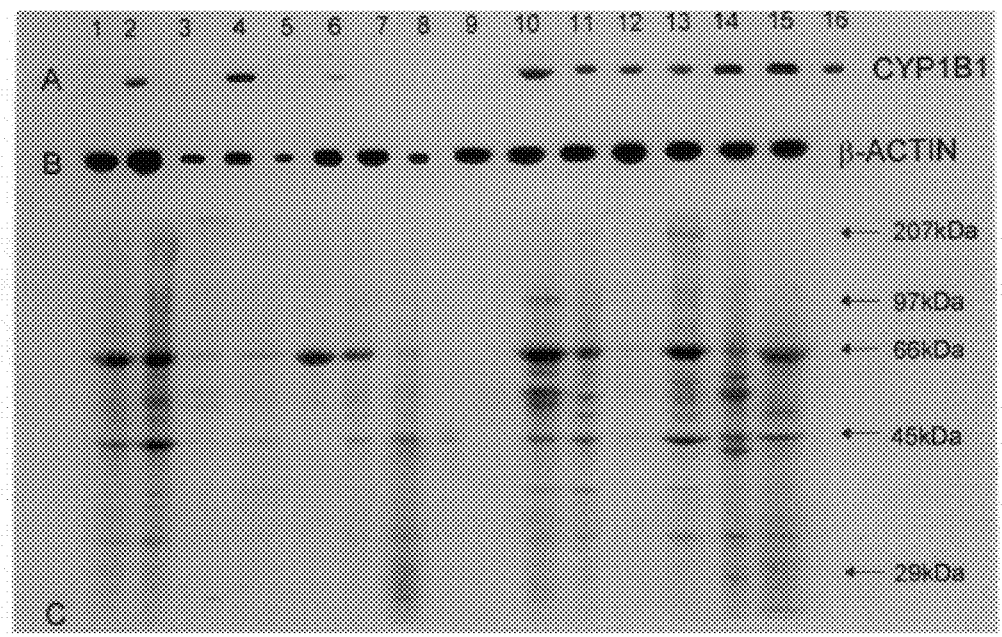
FIG. 3 shows and immunoblot of CYP1B1 in different types of tumours and normal tissues.

FIG. 3 shows an immunoblot of CYP1B1 in different types of tumours and normal tissues. Lane 1 normal colon, lane 2 colon adenocarcinoma, lane 3 normal kidney, lane 4 carcinoma of kidney, lane 5 normal breast, lane 6 breast cancer, lane 7 normal jejunum, lane 8 normal stomach, lane 9 normal liver, lane 10 malignant mixed Müllerian tumour, lane 11 endometrial adenocarcinoma, lane 12 ovarian carcinoma, lane 13 diffuse B cell lymphoma, lane 14 transitional cell carcinoma, lane 15 lung carcinoma, lane 16 positive control (dioxin-induced ACHN kidney tumour cells (panel A only). In panel B, the same series of tissue samples have been immunoblotted for β-actin, which is present in all normal and tumour samples. A Coomassie blue stained polyacrylamide gel of the same series of tissue samples displayed no evidence of protein degradation. The results demonstrated that this P450 is specifically localised to tumour cells, and that there is no CYP1B1 immunoreactivty in normal tissues.

TABLE 1

CYP1B1 Expression in Tumour Tissues and Normal Tissues.

| Tissue | Normal no pos./ no tested | Tumor no pos./ no tested | Histopathological diagnosis |
|---|---|---|---|
| Bladder | 0/8 | 8/8 | transitional cell carcinoma |
| Brain | 0/12 | 11/12 | astrocytoma |
| Breast | 0/10 | 12/12 | invasive ductal carcinoma |
| Colon | 0/10 | 11/12 | adenocarcinoma |
| Connective tissue | 0/9 | 8/9 | sarcoma |
| Kidney | 0/11 | 11/11 | clear cell carcinoma n = 10; transitional cell carcinoma n = 1 |
| Liver | 0/8 | not tested | not tested |
| Lung | 0/8 | 7/8 | squamous carcinoma |
| Lymph node | 0/5 | 9/9 | non-Hodgkin's lymphoma |
| Oesophagus | 0/8 | 8/8 | squamous carcinoma |
| Ovary | not tested | 7/7 | adenocarcinoma |
| Skin | 0/6 | 6/6 | squamous carcinoma |
| Small Intestine | 0/5 | not tested | not tested |
| Stomach | 0/10 | 9/10 | adenocarcinoma |
| Testis | 0/8 | 14/14 | malignant germ cell tumours |
| Uterus | 0/5 | 7/7 | adenocarcinoma n = 5; malignant mixed Mullerian tumour n = 2 |
| Total | 0/123 | 128/133 | |

EXAMPLE 4

Experiments were conducted to defect CYP1B1 RNA in various tumour and normal tissues.

Reverse transcription polymerase chain reaction (RT-PCR) experiments to detect CYP1B1 mRNA were carried out as described in McKay et al (23). RNA was extracted from tissue samples and cDNA was synthesised from the isolated RNA using oligo (dT). The CYP1B1 primers had the following sequences: Forward 5'-AAC TCT CCA TCA GGT GAG GT-3' (nt 2104–2123); Reverse 5'-TAA GGA AGT ATA CCA GAA GGC-3' (nt 2573–3593) giving a PCR product of 489 bp. β-actin was used as a positive control to confirm the presence and integrity of mRNA in each sample and the β-actin primers which were brought from Stratagene (Cambridge, UK) had the following sequences: Forward 5'-TGA CGG GGT CAC CCA CAC TGT GCC CAT CTA-3' (nt 1067–1105); Reverse 5'-CTA GAA GCA TTT GCG GTG GAC GAT GGA GGG-3' (nt 1876–1905). PCR with 35 cycles of amplification for both CYP1B1 and β-actin was performed as described (23). The positive control for CYP1B1 was a 2.78 kb CYP1B1 cDNA and the negative control was sterile water in place of cDNA. After PCR 10 μl of the PCR product was electrophoresed on a 1.5% agarose gel which incorporated 0.007% w/v ethidium bromide and visualized by UV illumination. The CYP1B1 PCR product was sequenced, after purification, by the direct dideoxy sequencing technique with a T7 sequencing kit (Pharmacia, Milton Keynes, UK) used according to the manufacturer's protocol. To further investigate the relative amount of CYP1B1 mRNA in normal and tumour tissues, semi-quantitative RT-PCR of normal and tumour kidney samples was performed using serial dilution of cDNA (24). β-actin mRNA was used as an internal control (29).

Figure 4:
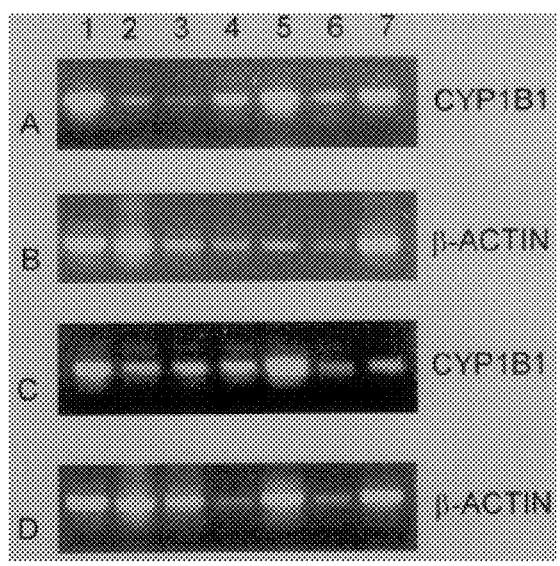
FIG. 4 shows CYP1B1 and $\beta$-actin mRNA in normal (A and B) and corresponding tumour (C and D) samples which have been detected by RT-PCR.

FIG. 4 shows CYP1B1 and β-actin mRNA in normal (A and B) and corresponding tumour (C and D) samples which have been detected by RT-PCR. Lane 1 kidney, lane 2 colon, lane 3 skin, lane 4 oesophagus, lane 5 stomach, lane 6 lymph node, lane 7 breast.

Analysis of the tumours by RT-PCR showed that all tumour samples in which CYP1B1 had been identified contained CYP1B1 mRNA. The PCR product was of the expected molecular size when analyzed by agarose gel eletrophoresis. Sequencing of the PCR product confirmed identity with CYP1B1.

Concluding remarks

The absence or low level of individual forms of P450 in most studies of human cancer (15–18), combined with extrapolation from studies of rodent hepatic carcinogenesis (25), had led to the general belief that tumour cells do not significantly express P450. However, we have now shown that CYP1B1 is expressed in a wide variety of malignant tumours of different histogenetic types and is not present in normal tissues, indicating that this P450 is a tumour specific form of P450. Tumours are composed of a variable proportion of tumour cells and non-tumour cells. To identify that a protein is tumour specific, it is important to demonstrate that the protein is localised only to tumour cells. Immunohistochemistry allows the direct visualisation of tumour cells and has the spatial resolution to separate tumour cells from non-tumour cells. Furthermore, it is important to show there has been no differential degradation of proteins in normal tissue samples compared with tumour samples and immunoblotting for β-actin (as a positive control protein) showed it to be present in every normal and tumour sample indicating there was no protein degradation. In addition, Coomassie blue staining of the polyacrylamide gels showed no evidence of protein degradation. Moreover, immunohistochemistry of the tumour samples provides its own internal control as sections of tumour contain non-tumour cells.

References

1. T. R. Sutter et al., *J. Biol. Chem.* 269, 10392 (1994)
2. S. A. Wrighton and J. C. Stevens, *Crit. Rev. Toxicol.* 22, 1 (1992)
3. D. R. Nelson et al, *Pharmacogenetics* 6, 1 (1996)
4. T. Shimada and F. P. Guengerich, *Chem. Res. Toxicol.* 4, 391 (1991); V. Nedelcheva and I. Gut, *Xenobiotica* 24, 1151 (1994); B. K. Park, M. Pirmohamed, N. R. Kitteringham, *Pharmac. Ther.* 58, 385 (1995).
5. J. H. Capdevila, J. R. Falck, R. W. Estabrook, *FASEB J.* 6, 731 (1992)
6. W. L. Miller, *Endocrine Rev.* 9, 295 (1988)
7. E. H. Oliw, *Prog. Lipid Res.* 33, 329 (1994)
8. G. I. Murray and M. D. Burke, *Biochem. Pharmacol.* 50, 895 (1995); L. S. Kaminsky and M. J. Fasco, *Crit. Rev. Toxicol.* 21, 407 (1992); E. G. Scheutz et al., *Arch. Biochem. Biophys.* 294, 206 (1992)
9. A. K. Jaiswal, F. J. Gonzalez, D. W. Nebert, *Science* 228, 80 (1985)
10. A. K. Jaiswal, D. W. Nebert, F. J. Gonzalez, *Nucl. Acid Res.* 14, 6773 (1986)
11. D. Sesardic, M. Pasanen, O. Pelkonen, *Carcinogenesis* 11, 1183 (1990)
12. H. Schweikl et al., *Pharmacogenetics* 3, 239 (1993)
13. F. J. Gonzalez and H. V. Gelboin, *Drug Metab. Rev.* 26, 165 (1994); F. P. Guengerich, *Cancer Res.* 48, 2946 (1988); K. Kawajiri and Y. Fujii-Kuriyama, *Jpan. J. Cancer Res.* 82, 1325 (1991); F. P. Guengerich, *Pharmac. Ther.* 54, 17 (1992)
14. G. A. Le Blanc and D. J. Waxman, *Drug Metab. Rev.* 20, 395 (1989); K. T. Kivisto, H. K. Kroemer, M. Eichelbaum, *Brit. J. Clin. Pharmacol.* 40, 523 (1995)
15. N. Albin et al., *Cancer Res.* 53, 3541 (1993)
16. C. Toussaint et al., *Cancer Res.* 53, 4606 (1993); M. Czerwinski et al., *Cancer Res.* 54, 1085 (1994)
17. W. H. M. Peters et al., *Gastroenterology* 103, 448 (1992); I. de Waziers et al., *Carcinogenesis* 12, 905 (1991); L. Massad et al., *Cancer Res.* 52, 6567 (1992); K. Mekhail-Ishak et al., *Cancer Res.* 49, 4866 (1989)
18. F. Janot et al., *Carcinogenesis* 14, 1279 (1993)
19. G. I. Murray et al., *Br. J. Cancer* 63, 1021 (1991); G. I. Murray et al., *J. Pathol.* 171, 49 (1993); G. I. Murray et al., *Gut* 35, 599 (1994)
20. R. J. WeaveR et al., *Biochem. Pharmacol.* 47, 763 (1994)
21. J. A. McKay et al., *J. Histochem. Cytochem.* 43, 615 (1995)
22. D. C. Spink et al., *Arch. Biochem. Biophys.* 293, 242–348 (1992)
23. J. A. McKay et al., *FEBS Letts.* 374, 270 (1995)
24. M. J. Dallman and A. C. G. Porter, In *PCR, A practical approach*, eds. J. McPherson, P. Quirke and G. R. Taylor (IRL Press, Oxford) p 215–224.
25. A. Buchmann et al., *Carcinogenesis* 6, 513 (1985); M. W. Roomi, R. K. Ho, D. S. R. Sarma, E. Farber, *Cancer Res.* 45, 564 (1985); A. Buchmann et al., *Cancer Res.* 47, 2911 (1987)
26. T. G. Krontiris, *N. Engl. J. Med.* 333, 303 (1995); L. M. Ponz de Leon, *Recent Res. Cancer Res.* 136, 35 (1994); S. K. Bahra, B. K. A. Rasheed, S. H. Bigner, D. D. Bigner, *Lab. Invest.* 71, 621 (1994)
27. G. L. Wang, B-H, Jiang, E. A. Rue, G. L. Semenza, *Proc. Natl. Acad. Sci. USA* 92, 5510 (1995)
28. J. P. Whitlock et al., *FASEB. J.* 10, 809 (1996)
29. T. Horishika et al, *Cancer Res.* 52,108 (1992)
30. Harlow et al., *Antibodies—A Laboratory Manual,* Cold Spring Harbor, Cold Spring Harbor, NY (1988)
31. Otto et al., *Endocrinology* 129:970–982 (1991)
32. Weaver et al. *Biochem. Pharmacol.* 46:1183–1197 (1993)
33. Laemmli, *Nature* 227:68 (1970)
34. Lowry, *J. Biol. Chem.* 193:265 (1951)
35. Towbin et al. *Proc. Natl. Acad. Sci. USA* 76:4350 (1979)
36. J. R. Willimson, *Nature* 382:112–113 (1996)
37. A. D. Ellington et al, *Nature* 346:818–822 (1990)

What is claimed is:

1. A method for determining the presence of cancer cells in a sample of tissue or cells from a human patient, the method comprising contacting CYP1B1 protein from said sample of said patient with an antibody for human cytochrome P450 CYP1B1, and detecting binding of the antibody to human CYP1B1 protein in said sample, wherein a greater amount of the binding of said antibody to said human CYP1B1 protein in said sample as compared to normal control cells is an indication of the presence of cancer cells in said sample.

2. The method of claim 1, further comprising the steps of obtaining from the patient the tissue sample to be tested for the presence of cancer cells; and producing a prepared sample in a sample preparation process prior to contacting the prepared sample with a CYP1B1 antibody.

3. The method of claim 2 wherein binding of the antibody to CYP1B1 protein in sample is detected by immunohistochemical analysis.

4. The method of claim 3, wherein the sample preparation process comprises contacting the tissue with a fixative and producing a thin section suitable for immunohistochemical analysis.

5. The method of claim 4, wherein the fixative is formalin.

6. The method of claim 4, wherein the thin section is wax-embedded.

7. The method of claim 3, wherein the immunohistochemical analysis comprises a conjugated enzyme labelling technique.

8. The method of claim 2, wherein the sample preparation process comprises tissue homogenization.

9. The method of claim 8, wherein the sample preparation process further comprises isolating microsomes.

10. The method of claim 8, wherein the binding of the antibody to the CYP1B1 protein in a prepared sample is detected by Western blot analysis.

11. The method of claim 10, wherein the Western blot analysis comprises a conjugated enzyme labelling technique.

12. The method of claim 8, wherein the binding of the antibody to the CYP1B1 protein in the prepared sample is detected by an immunoassay.

13. The method of claim 12, wherein the immunoassay is selected from the group consisting of antibody capture assay, two-antibody sandwich assay and antigen capture assay.

14. The method of claim 12, wherein the immunoassay is a solid support-based immunoassay.

15. The method of claim 12, wherein the immunoassay comprises a conjugated enzyme labelling technique.

16. The method of claim 1, wherein the antibody is a polyclonal antibody.

17. The method of claim 1, wherein the antibody is a monoclonal antibody.

18. The method of claim 1, wherein the antibody recognizes a preselected epitope of the CYP1B1 protein.

19. The method of claim 1, wherein the antibody is specific for CYP1B1 protein.

20. The method of claim 1, wherein the tissue sample is selected from the group consisting of bladder, brain, breast, colon, connective tissue, kidney, lung, lymph node, oesophagus, ovary, skin, stomach, testis, and uterus.

* * * * *